US008124594B2

(12) United States Patent  
Purpura et al.

(10) Patent No.: US 8,124,594 B2
(45) Date of Patent: Feb. 28, 2012

(54) METHODS USING PHOSPHATIDYLSERINE, LYSOPHOSPHATIDYLSERINE, AND/OR SALTS THEREOF TO INCREASE TESTOSTERONE LEVELS

(75) Inventors: Martin Purpura, Milwaukee, WI (US); Ralf Jäger, Milwaukee, WI (US); Scott L. Hagerman, North Oaks, MN (US)

(73) Assignee: Chemi Nutra, LLC, White Bear Lake, MN (US)

( * ) Notice: Subject to any disclaimer, the term of this patent is extended or adjusted under 35 U.S.C. 154(b) by 0 days.

(21) Appl. No.: 12/325,225

(22) Filed: Nov. 30, 2008

(65) Prior Publication Data
US 2009/0143339 A1 Jun. 4, 2009

Related U.S. Application Data

(60) Provisional application No. 61/004,999, filed on Nov. 30, 2007.

(51) Int. Cl.
*A61K 31/685* (2006.01)
(52) U.S. Cl. .................................. 514/109; 514/121
(58) Field of Classification Search .................. None
See application file for complete search history.

(56) References Cited

U.S. PATENT DOCUMENTS

| 4,089,801 | A | * | 5/1978 | Schneider ........................ 264/4.1 |
| 6,632,671 | B2 | | 10/2003 | Unger |
| 6,673,378 | B1 | | 1/2004 | Fritz |
| 6,878,532 | B1 | | 4/2005 | Meyer |
| 7,049,107 | B1 | | 5/2006 | Meyer |
| 7,199,112 | B2 | | 4/2007 | Llewellyn |
| 2004/0137071 | A1 | | 7/2004 | Unger |
| 2004/0234544 | A1 | | 11/2004 | Jager et al. |
| 2007/0066567 | A1 | | 3/2007 | Llewellyn |

FOREIGN PATENT DOCUMENTS

| WO | 02/051426 | * | 7/2002 |
| WO | 2006/060325 | * | 6/2006 |
| WO | WO 2008/120214 A2 | | 10/2008 |
| WO | WO 2008/120214 A3 | | 12/2008 |

OTHER PUBLICATIONS

Alves et al., "Phosphatidylserine reverses reserpine-induced amnesia," 2000 *Eur. J. Pharmacol.* 404:161-167.
Blokland et al., "Cognition-enhancing properties of subchronic phosphatidylserine (PS) treatment in middle-aged rats: comparison of bovine cortex PS with egg PS and soybean PS," Oct. 1999 *Nutrition* 15(10):778-783.
Casamenti et al., "Effect of phosphatidylserine on acetylcholine output from the cerebral cortex of the rat," 1979 J. Neurochem. 32(2):529-533.
Chen and Li, "Comparison of molecular species of various transphosphatidylated phosphatidylserine (PS) with bovine cortex PS by mass spectrometry," 2008 *Chemistry and Physics of Lipids* 152:46-56. Available online Jan. 8, 2008.
Colao et al., "Increased prevalence of thyroid autoimmunity in patients successfully treated for Cushing's disease," Jul. 2000 *Clin. Endocrinol.* 53(1):13-19.
Delwaide et al., "Double-blind randomized controlled study of phosphatidylserine in senile demented patients," 1986 *Acta Neurol. Scand.* 73(2):136-140.
Engel et al., "Double-blind cross-over study of phosphatidylserine vs. placebo in patients with early dementia of the Alzheimer type," 1992 *Eur. Neuropsychopharmocol.* 2(2):149-155.
Fahey and Pearl, "The hormonal and perceptive effects of phosphatidylserine administration during two weeks of resistive exercise-induced overtraining," *Biology of Sport* 1998, 15(3):135-144.
Feldman et al., "Age trends in the level of serum testosterone and other hormones in middle-aged men: longitudinal results from the Massachusetts male aging study," Feb. 2002 *J. Clin. Endocrinol. Metab.* 87(2):589-598.
Fry et al., "Monitoring exercise stress by changes in metabolic and hormonal responses over a 24-h period," *Eur J Appl Physiol* 1991, 63:228-234.
Fry et al., "Pituitary-adrenal-gonadal responses to high-intensity resistance exercise overtraining," Dec. 1998 *J. Appl. Physiol.* 85(6):2352-2359.
Harman et al., "Longitudinal effects of aging on serum total and free testosterone levels in healthy men," 2001 *J. Clin. Endocrinol. Metab.* 86(2):724-731.
Hashimoto et al., "Low plasma corticotropin-releasing hormone (CRH) levels in patients with non-insulin dependent diabetes mellitus (NIDDM)" Dec. 1993 *Endocr. J.* 40(6):705-709.
Hellhammer et al., "Effects of soy lecithin phosphatidic acid and phosphatidylserine complex (PAS) on the endocrine and psychological responses to mental stress," Jun. 2004 *Stress* 7(2):119-126.
Hirata and Axelrod, "Phospholipid methylation and biological signal transmission," Sep. 5, 1980 *Science* 209:1082-1090.
"Hypogonadism," *Wikipedia, The Free Encyclopedia* Available online [retrieved on Nov. 28, 2008]. Retrieved from the Internet: <en.wikipedia.org/wiki/Hypogonadism>; 5 pgs. Last modified Nov. 28, 2008.
International Search Report and Written Opinion for PCT/US2008/085092; mailed Mar. 4, 2009.
Izquierdo et al., "Detraining and tapering effects on hormonal responses and strength performance," *Journal of Strength and Conditioning Research* 2007, 21(3):768-775.
Jäger et al., "Phospholipids and sports performances," *J. Int. Soc. Sports Nutrition* Jul. 25, 2007; 4:5-12.
Jorissen et al., "Safety of soy-derived phosphatidylserine in elderly people," Oct. 2002 *Nutr. Neurosci.* 5(5):337-343.
Kingsley et al., "Effects of phosphatidylserine on oxidative stress following intermittent running," Aug. 2005 *Med. Sci. Sports Exerc.* 37(8):1300-1306.
Kingsley et al., "Effects of phosphatidylserine on exercise capacity during cycling in active males," Jan. 2006 *Med. Sci. Sports Exerc.* 38(1):64-71.
Monteleone et al., "Effects of phosphatidylserine on the neuroendocrine response to physical stress in humans," 1990 *Neuroendocrinology* 52:243-248.

(Continued)

*Primary Examiner* — Phyllis G. Spivack
(74) *Attorney, Agent, or Firm* — Mueting, Raasch & Gebhardt, P.A.

(57) ABSTRACT

Methods using phosphatidylserine, lysophosphatidylserine, and/or salts thereof to increase testosterone levels in subjects in need thereof are disclosed herein. The methods can be useful for subjects having age related decline in testosterone, exercise induced decline in testosterone, and/or hypogonadism.

13 Claims, 1 Drawing Sheet

OTHER PUBLICATIONS

Monteleone et al., "Blunting by chronic phosphatidylserine administration of the stress-induced activation of the hypothalamo-pituitary-adrenal axis in healthy men," *European J Clin Pharmacol* 1992, 42:385-388.

Navar, "Optimizing testosterone levels in aging men," *Life Extension* Jul. 2008, pp. 37-39.

Perry et al., "Behavioural and neurochemical effects of phosphatidylserine in MPTP lesion of the substantia nigra of rats," 2004 *Eur. J. Pharmacol.* 484:225-233.

Putignano et al., "Alterations in serum protein levels inpatients with Cushing's syndrome before and after successful treatment," Sep. 2000 *J. Clin. Endocrinol. Metab.* 85(9):3309-3312.

Singh et al., "Differential hypothalamic-pituitary-adrenal axis reactivity to psychological and physical stress," Jun. 1999 *J. Clin. Endocrinol. Metab.* 84(6):1944-1948.

Starks et al., "The effects of phosphatidylserine on endocrine response to moderate intensity exercise," *J. Int. Soc. Sports Nutrition* Jul. 28, 2008; 5:11-16.

"Study proves: Beneficial effects of phosphatidylserine (PS) on stress managements," *CHEMI Nutra News Release* Jul. 28, 2008. 2 pages.

"Testosterone," *Wikipedia, The Free Encyclopedia* Available online [retrieved on Nov. 28, 2008]. Retrieved from the Internet: <en.wikipedia.org/wiki/Testosterone>; 11 pgs. Last modified Nov. 25, 2008.

"Testosterone therapy: can it help older men feel young again?" MayoClinic.com [online]. Mayo Foundation for Medical Education and Research; Rochester, MN. Apr. 12, 2008. [retrieved on Oct. 7, 2008]. Retrieved from the Internet: <www.mayoclinic.com/health/testosterone-therapy/MC00030>; 3 pgs.

Vannucchi and Pepeu, "Effect of phosphatidylserine on acetylcholine release and content in cortical slices from aging rats," Sep.-Oct. 1987 *Neurobiol. Aging* 8(5):403-407.

Welsh et al., "Mechanism of glucocorticoid-induced suppression of testicular androgen biosynthesis in vitro," Dec. 1982 *Biol. Reproduc.* 27(5):1138-1146.

Wolkowitz and Reus, "Treatment of depression with antiglucocorticoid drugs," Sep.-Oct. 1999 *Psychosom. Med.* 61(5):698-711.

"Can you get phosphatidylserine from food sources?," Answers.com, WikiAnswers [retrieved on Apr. 19, 2010], retrieved from the internet <URL: http://wiki.answers.com/Q/Can_you_get_phosphatidylserine_from_food_sources>; 4 pgs; Apr. 2010.

Fernholz, "The effectes of phosphatidylserine on markers of muscular stress in endurance runners," Master's Thesis, St. Cloud State University, St. Cloud, MN, May 2000.

Hakkinen et al., "Serum hormone concentrations during prolonged training in elite endurance-trained and strength-trained athletes," Oct. 1989 *Eur. J. Appl. Physiol. Occup. Physiol.* 59(3):233-238.

Shurtleff et al., "What is Soy Lecithin?," [retrieved on Apr. 19, 2010]. Retrieved from the Internet:<URL:http://www.soyinfocenter.com/HSS/lecithin1.php/>; 7 pgs.; 2007.

"Structure / Function claims and qualified health claims for SerinAid® PhosphatidylSerine (PS)" technical datasheet. CHEMI Nutra, Inc.: White Bear Lake, MN, Oct. 28, 2008; 3 pgs.

Starks, Michael, "The effects of a 600 mg dose of soy phosphatidylserine on cortisol, growth hormone and testosterone response to moderate intensity exercise," Ph.D. thesis, University of Mississippi, Cover Date Dec. 2007.

"Ingestion", Wikipedia, last modified Sep. 1, 2011, (retrieved on Mar. 14, 2011]. Retrived from the Internet: <URL: http//en.wikipedia.org/wiki/ingestionn>; 1 pg.

"Oral Administration", Wikipedia, last modified Feb. 4, 2011, (retrieved on Mar. 14, 2011]. Retrived from the Internet: <URL: http://en.wikipedia.org/wiki/oral-administration>; 1 pg.

"Sublingual and Buccal Medication Administration", Encyclopedia of Nursing and Allied Health, 2011, [retrieved on Mar. 14, 2011]. Retrieved from the Internet: <URL:http://www.enotes.com/nursing-encyclopedia/sublingual-buccal-medication-administration>: 2 pgs.

\* cited by examiner

METHODS USING PHOSPHATIDYLSERINE, LYSOPHOSPHATIDYLSERINE, AND/OR SALTS THEREOF TO INCREASE TESTOSTERONE LEVELS

This application claims the benefit of U.S. Provisional Application No. 61/004,999, filed Nov. 30, 2007, which is incorporated herein by reference in its entirety.

BACKGROUND

Testosterone is a hormone that is formed in the testes of males, the ovaries of females, and the adrenal glands. In both sexes, testosterone plays a key role in health and well-being with increased energy, strength, stimulation of red blood cell production, growth, and protein synthesis. Males, beginning at puberty, produce from about forty to sixty times as much testosterone as females, although females are more sensitive to the hormone.

Testosterone levels can vary from normal for a variety of reasons, often resulting in less than optimal levels of testosterone. For example, some young men can be hypogonadal. Further, with aging and beginning in the mid thirties, testosterone production in males gradually decreases until at the age of 80, when levels are only about 20% of the level for a normal young man. Finally, although exercise is known to be beneficial in maintaining vitality, stress resulting from early stages of overtraining may cause stress, which can result in, among other things, sore muscles, increased heart rate, and lowered testosterone levels. The advantages of testosterone can be lost with lowered testosterone levels, leading to a variety of undesirable symptoms.

Hormone replacement therapy has long been recommended for post menopausal women and some doctors recommend testosterone replacement for older men or for young men with less than optimal levels of testosterone. Testosterone is a strictly regulated, Schedule 3 substance and can be administered only through a physician's prescription. Oral testosterone is partly converted to an inactive 7-α-methyl metabolite on first pass through the liver. Injectable testosterone is the preferred mode of treatment but requires a visit to a physician's office or clinic. Generally, about 100 mg per week can be prescribed for injection to males with testosterone levels less than 350 nanograms per deciliter.

The need remains for alternative methods for raising testosterone levels for subjects in need thereof.

SUMMARY

In one embodiment, the present disclosure provides a method for increasing the testosterone level of a subject (e.g., a human male) having an age related decline in testosterone. The method includes administering to the subject in need thereof a therapeutically effective amount of a composition including a lipid selected from the group consisting of phosphatidylserine (e.g., phosphatidylserine derived from soy), a salt of phosphatidylserine, lysophosphatidylserine, a salt of lysophosphatidylserine, and combinations thereof.

In another embodiment, the present disclosure provides a method for increasing the testosterone level of a subject (e.g., a human male) having an exercise induced decline in testosterone. The method includes administering to the subject in need thereof a therapeutically effective amount of a composition including a lipid selected from the group consisting of phosphatidylserine (e.g., phosphatidylserine derived from soy), a salt of phosphatidylserine, lysophosphatidylserine, a salt of lysophosphatidylserine, and combinations thereof.

In still another embodiment, the present disclosure provides a method for increasing the testosterone level of a subject (e.g., a human male) having hypogonadism. The method includes administering to the subject in need thereof a therapeutically effective amount of a composition including a lipid selected from the group consisting of phosphatidylserine (e.g., phosphatidylserine derived from soy), a salt of phosphatidylserine, lysophosphatidylserine, a salt of lysophosphatidylserine, and combinations thereof.

Definitions

The term "comprises" and variations thereof do not have a limiting meaning where these terms appear in the description and claims.

As used herein, "a," "an," "the," "at least one," and "one or more" are used interchangeably.

As used herein, the term "or" is generally employed in the sense as including "and/or" unless the context of the usage clearly indicates otherwise.

Also herein, the recitations of numerical ranges by endpoints include all numbers subsumed within that range (e.g., 1 to 5 includes 1, 1.5, 2, 2.75, 3, 3.80, 4, 5, etc.).

The above summary is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

DETAILED DESCRIPTION OF ILLUSTRATIVE EMBODIMENTS

Figure 1:
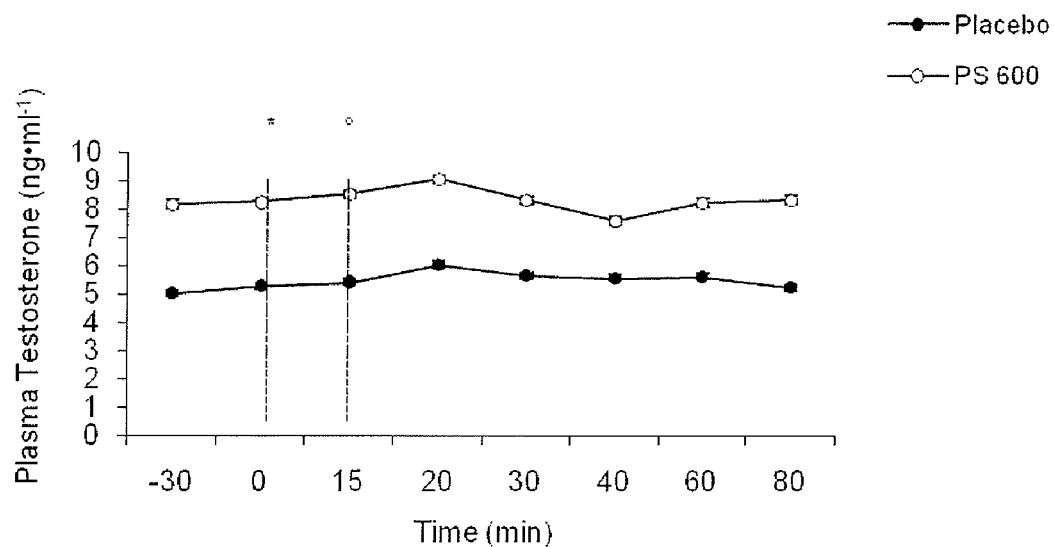
FIG. 1 illustrates plasma testosterone response to exercise (pre-exercise phase −30 to 0 minutes, exercise phase: 0 to 15 minutes, recovery phase 16 to 80 minutes) between groups after 10 days of oral treatment with placebo or 600 mg per day soy-derived phosphatidylserine (S-PS) for healthy volunteers.

Testosterone levels can vary from normal for a variety of reasons, resulting in less than optimal levels of testosterone. The present disclosure provides methods for increasing the testosterone level of a subject in need thereof. The method includes administering to the subject in need thereof a therapeutically effective amount of a composition including a lipid selected from the group consisting of phosphatidylserine (e.g., phosphatidylserine derived from soy), a salt of phosphatidylserine, lysophosphatidylserine, a salt of lysophosphatidylserine, and combinations thereof. As used herein, the phrase "therapeutically effective amount" as applied to administering a composition including a lipid is intended to mean that the amount of lipid (e.g., phosphatidylserine, lysophosphatidylserine, and/or salts thereof) administered is effective to achieve the desired result (e.g., a detectable or substantial increase in free and/or total testosterone level). In certain embodiments, administering to a subject a therapeutically effective amount of a composition including a lipid (e.g., phosphatidylserine, lysophosphatidylserine, and/or salts thereof) can result in an increase in testosterone level for the subject of at least 10%, at least 15%, at least 20%, at least 25%, at least 30%, at least 35%, at least 40%, at least 45%, at least 50%, or even higher.

Phosphatidylserine is a naturally occurring phospholipid. Phospholipids (PL) are naturally occurring components of bodily tissues, in particular cell membranes. The proper balance of synthesis within the body and ingestion from the diet is vital to maintaining membrane health, and general structural health of the body. In addition, several of phospholipids have regulatory functions. The phospholipid phosphatidylserine (PS) is most concentrated in organs with a high metabolic activity, such as the brain, lungs, heart, liver, and skeletal muscle. Phosphatidylserine has been found to modulate the activity of receptors ion channels, enzymes, and signaling molecules, as well as being involved in governing membrane fluidity. In order to optimize certain of these functions, phosphatidylserine supplements may be recommended. Traditionally, these supplements have been derived from bovine cerebral cortex; however due to the potential transfer of infectious diseases, soy-derived phosphatidylserine has been introduced as a safe alternative. Phosphatidylserine has been shown to improve a variety of brain functions which tend to decline with age. Phosphatidylserine has been reported to be an effective supplement for combating exercise induced stress and preventing the physiological deterioration that can come with too much exercise. Phosphatidylserine has been reported to attenuate serum cortisol and ACTH responses to staged cycling exercise. In one study (Monteleone et al., *European J Clin Pharmacol* 1992, 41:385-388), 800 mg phosphatidylserine supplementation lowered cortisol response by 30%, whereas 400 mg showed no significant result compared to placebo. In another study (Fahey et al., *Biology of Sport* 1998, 15:135-144), 800 mg of phosphatidylserine was reported to reduce the cortisol response to intensive resistance training by 20%, but had no effect on testosterone levels. Following these studies, the effective dose for cortisol reduction has been set at 800 mg/day for short term (10-15 days) administration.

A preferred phosphatidylserine is derived from plants. A particularly preferred phosphatidylserine is derived from soy. A composition including a lipid such as phosphatidylserine, lysophosphatidylserine, and/or salts thereof can, and frequently does, include other phospholipids such as phosphatidylcholine. When an amount of lipid (e.g., phosphatidylserine, lysophosphatidylserine, and/or salts thereof) is recited herein, it refers to amount of phosphatidylserine, lysophosphatidylserine, and/or salts thereof that are present, regardless of the presence of other phospholipids.

Age Related Decline in Testosterone.

In one embodiment, the present disclosure provides a method for increasing the testosterone level of a subject, preferably a human male, having an age related decline in testosterone. The method includes administering to the subject in need thereof a therapeutically effective amount of a composition including a lipid selected from the group consisting of phosphatidylserine (e.g., phosphatidylserine derived from soy), a salt of phosphatidylserine, lysophosphatidylserine, a salt of lysophosphatidylserine, and combinations thereof.

With aging, and beginning in the mid thirties, testosterone production in males gradually decreases until at the age of 80, when levels are only about 20% of the level for a normal young man. See, for example, Feldman et al., *J Clin Endocrinol Metab* 2002, 87:589-598 (finding testosterone cross-sectionally declining at 0.8% per year (total testosterone) and 2% per year (free testosterone). See also, Haiman et al., *J Clin Endocrinol Metab* 2001, 86:724-731; and Wikipedia contributors, 'Testosterone', *Wikipedia, The Free Encyclopedia*, 25 Nov. 2008, 07:04 UTC. With this decline, the advantages of testosterone are lost, leading to a number of disturbing symptoms such as loss of stamina, strength and lean muscle mass, and reduced libido. Some studies indicate that anxiety, depression and cognitive decline are associated with lowered testosterone.

As used herein, a subject having an age related decline in testosterone is intended to refer to a subject (e.g., a human male) over the age of 35 and having a testosterone level substantially lower than 600 nanograms/deciliter total testosterone (e.g., an average total testosterone level for a 35 year old human male). In certain embodiments, the subject can be a human male over the age of 40 and having a testosterone level substantially lower than 550 nanograms/deciliter total testosterone. As used herein, "substantially lower" testosterone levels mean that the testosterone levels are at least 1% lower, at least 2% lower, at least 5% lower, at least 10% lower, at least 15% lower, at least 20% lower, at least 25% lower, at least 30% lower, at least 35% lower, at least 40% lower, at least 45% lower, or at least 50% lower than the average value being compared. Testosterone levels can be identified using a simple blood test performed by a laboratory.

Phosphatidylserine, lysophosphatidylserine, and/or salts thereof can be administered to a subject having an age related decline in testosterone by a variety of methods including, for example, oral administration, intraveneous (IV) administration, parenteral administration, or a combination thereof. Preferably, phosphatidylserine, lysophosphatidylserine, and/or salts thereof are administered by oral administration.

Phosphatidylserine, lysophosphatidylserine, and/or salts thereof can be administered to a subject having an age related decline in testosterone at a convenient daily dosage. In certain embodiments, at most 600 mg per day of phosphatidylserine, lysophosphatidylserine, and/or salts thereof are administered to the subject. In certain embodiments, at least 100 mg per day of phosphatidylserine, lysophosphatidylserine, and/or salts thereof are administered to the subject. In certain embodiments, 500 mg per day of phosphatidylserine, lysophosphatidylserine, and/or salts thereof are administered to the subject. In certain embodiments, 400 mg per day of phosphatidylserine, lysophosphatidylserine, and/or salts thereof are administered to the subject. In certain embodiments, 300 mg per day of phosphatidylserine, lysophosphatidylserine, and/or salts thereof are administered to the subject. In certain embodiments, 200 mg per day of phosphatidylserine, lysophosphatidylserine, and/or salts thereof are administered to the subject.

The daily dosage of phosphatidylserine, lysophosphatidylserine, and/or salts thereof to a subject having an age related decline in testosterone can be administered in a single dose. Alternatively, the daily dosage of phosphatidylserine, lysophosphatidylserine, and/or salts thereof can be administered in multiple doses. For example, in certain embodiments phosphatidylserine, lysophosphatidylserine, and/or salts thereof are administered in at least two doses per day. For another example, in certain embodiments phosphatidylserine, lysophosphatidylserine, and/or salts thereof are administered in at least three doses per day.

Phosphatidylserine can be administered to a subject having an age related decline in testosterone for a convenient treatment period. In certain embodiments, phosphatidylserine can be administered to the subject for at least a one day treatment period. In certain other embodiments, phosphatidylserine can be administered to the subject for at least a 2 day, at least a 3 day, at least a 4 day, at least a 7 day, or at least a 10 day treatment period. In certain embodiments the treatment period can continue as needed (e.g., for life). In certain embodiments, phosphatidylserine can be administered to the subject for at most a one year treatment period. In certain other embodiments, phosphatidylserine can be administered to the subject for at most a 180 day, at most a 120 day, at most a 90 day, at most a 60 day, at most a 30 day, or at most a 15 day treatment period. In certain embodiments, phosphatidylserine can be administered to the subject for a 10 to 15 day treatment period.

Optionally, one or more exercise regimens as described herein can be implemented during at least a portion of the treatment period.

In certain embodiments, administration of phosphatidylserine, lysophosphatidylserine, and/or salts thereof to a subject having an age related decline in testosterone achieves an increase in testosterone (e.g., free testosterone and/or total testosterone) of at least 10%, at least 15%, at least 20%, at least 25%, at least 30%, at least 35%, at least 40%, at least 45%, at least 50%, or even higher than the testosterone level prior to administration of phosphatidylserine, lysophosphatidylserine, and/or salts thereof.

Exercise-Induced Decline in Testosterone.

In another embodiment, the present disclosure provides a method for increasing the testosterone level of a subject, preferably a human male, having an exercise induced decline in testosterone. The method includes administering to the subject in need thereof a therapeutically effective amount of a composition including a lipid selected from the group consisting of phosphatidylserine (e.g., phosphatidylserine derived from soy), a salt of phosphatidylserine, lysophosphatidylserine, a salt of lysophosphatidylserine, and combinations thereof.

Although exercise is known to be beneficial in maintaining vitality, stress resulting from early stages of overtraining may cause stress, resulting, for example, in sore muscles, increased heart rate, and lowered testosterone levels. The body has difficulty adjusting, but usually recovers with rest. Chronic overtraining often creates a disturbance in the anabolic-catabolic balance, which may express itself in decreased performance, injury, depressed immunity and psychological depression. See, also, Fry et al., *Eur J Appl Physiol* 1991, 63:228-234; and Izquierdo et al., *Journal of Strength and Conditioning Research* 2007, 21:768-775.

As used herein, a subject having an exercise induced decline in testosterone is intended to refer to a subject having a testosterone level (e.g., free testosterone and/or total testosterone), during and/or after exercise, that is substantially lower (e.g., that is at least 1% lower) than the testosterone level for the same subject under normal conditions (e.g., after 10 days of no exercise). In certain embodiments, the testosterone level, during and/or after exercise, is at least 2% lower, at least 5% lower, at least 10% lower, at least 15% lower, at least 20% lower, at least 25% lower, at least 30% lower, at least 35% lower, at least 40% lower, at least 45% lower, or at least 50% lower than the testosterone level for the same subject under normal conditions. Normal testosterone levels and testosterone levels during and/or after exercise can be identified using a simple blood tests performed by a laboratory.

Phosphatidylserine, lysophosphatidylserine, and/or salts thereof can be administered to a subject having an exercise induced decline in testosterone by a variety of methods including, for example, oral administration, intravenous (IV) administration, parenteral administration, or a combination thereof. Preferably, phosphatidylserine, lysophosphatidylserine, and/or salts thereof are administered by oral administration.

Phosphatidylserine, lysophosphatidylserine, and/or salts thereof can be administered to a subject having an exercise induced decline in testosterone at a convenient daily dosage. In certain embodiments, at most 600 mg per day of phosphatidylserine, lysophosphatidylserine, and/or salts thereof are administered to the subject. In certain embodiments, at least 100 mg per day of phosphatidylserine, lysophosphatidylserine, and/or salts thereof are administered to the subject. In certain embodiments, 500 mg per day of phosphatidylserine, lysophosphatidylserine, and/or salts thereof are administered to the subject. In certain embodiments, 400 mg per day of phosphatidylserine, lysophosphatidylserine, and/or salts thereof are administered to the subject. In certain embodiments, 300 mg per day of phosphatidylserine, lysophosphatidylserine, and/or salts thereof are administered to the subject. In certain embodiments, 200 mg per day of phosphatidylserine, lysophosphatidylserine, and/or salts thereof are administered to the subject.

The daily dosage of phosphatidylserine, lysophosphatidylserine, and/or salts thereof to a subject having an exercise induced decline in testosterone can be administered in a single dose. Alternatively, the daily dosage of phosphatidylserine, lysophosphatidylserine, and/or salts thereof can be administered in multiple doses. For example, in certain embodiments phosphatidylserine, lysophosphatidylserine, and/or salts thereof are administered in at least two doses per day. For another example, in certain embodiments phosphatidylserine, lysophosphatidylserine, and/or salts thereof are administered in at least three doses per day.

Phosphatidylserine, lysophosphatidylserine, and/or salts thereof can be administered to a subject having an exercise induced decline in testosterone for a convenient treatment period. In certain embodiments, phosphatidylserine, lysophosphatidylserine, and/or salts thereof can be administered to the subject for at least a one day treatment period. In certain other embodiments, phosphatidylserine, lysophosphatidylserine, and/or salts thereof can be administered to the subject for at least a 2 day, at least a 3 day, at least a 4 day, at least a 7 day, or at least a 10 day treatment period. In certain embodiments the treatment period can continue as needed (e.g., for life). In certain embodiments, phosphatidylserine, lysophosphatidylserine, and/or salts thereof can be administered to the subject for at most a one year treatment period. In certain other embodiments, phosphatidylserine, lysophosphatidylserine, and/or salts thereof can be administered to the subject for at most a 180 day, at most a 120 day, at most a 90 day, at most a 60 day, at most a 30 day, or at most a 15 day treatment period. In certain embodiments, phosphatidylserine, lysophosphatidylserine, and/or salts thereof can be administered to the subject for a 10 to 15 day treatment period.

Optionally, one or more exercise regimens as described herein can be maintained during at least a portion of the treatment period. Acute exercise induces dramatic metabolic and endocrinological changes, and the hormonal variation can be used to gauge predictive performance and physiological change. Studies have shown that exercise, especially anaerobic exercise (e.g. weight lifting) involving large muscle groups with high workloads, can increase the concentration of anabolic hormones, including testosterone. Initially testosterone levels rise in individuals who engage in vigorous anaerobic exercise bouts. However, testosterone levels often decline significantly in as little as two hours post exercise, and remain at lower levels over the remainder of the recovery period. Therefore, administration of phosphatidylserine, lysophosphatidylserine, and/or salts thereof during recovery from intense anaerobic exercise can reduce the post-exercise drop in testosterone. Strong adaptational changes realized through optimized exercise prescription could significantly benefit the individual.

The fatigue component can be a manifestation associated with acute exercise or associated with a state of chronic fatigue, where insufficient regeneration time would normally allow testosterone levels to resume to healthy, productive levels.

In certain embodiments, administration of phosphatidylserine, lysophosphatidylserine, and/or salts thereof to a subject having an exercise induced decline in testosterone achieves an increase in testosterone (e.g., free testosterone and/or total testosterone) of at least 10%, at least 15%, at least 20%, at least 25%, at least 30%, at least 35%, at least 40%, at least 45%, at least 50%, or even higher than the testosterone level prior to administration of phosphatidylserine, lysophosphatidylserine, and/or salts thereof.
Hypogonadism.

In still another embodiment, the present disclosure provides a method for increasing the testosterone level of a subject, preferably a human male, having hypogonadism. The method includes administering to the subject in need thereof a therapeutically effective amount of a composition including a lipid selected from the group consisting of phosphatidylserine (e.g., phosphatidylserine derived from soy), a salt of phosphatidylserine, lysophosphatidylserine, a salt of lysophosphatidylserine, and combinations thereof.

As discussed herein above, subjects can have lower than optimal testosterone levels due to a variety of conditions including, for example, age related decline in testosterone and exercise induced decline in testosterone. Further, subjects not suffering from age related decline in testosterone or exercise induced decline in testosterone can, nonetheless have lower than optimal testosterone levels as a result of, for example, hypogonadism.

Normal testosterone levels can be from 298 to 1098 nanograms/dl. As used herein, the term "hypogonadism" is used to refer to subjects having a total testosterone level of less than 400 nanogram s/dl, and in certain embodiments less than 350 nanograms/dl. Hypogonadism can be related, for example, to a defect of the reproductive system that results in lack of function of the gonads (e.g., the ovaries or the testes). Hypogonadism can result in symptoms including, but not limited to, fatigue, muscle loss, memory loss, poor libido, glucose intolerance, lipid abnormalities, depression, and anxiety. Testosterone levels can be identified using a simple blood test performed by a laboratory. See also, Wikipedia contributors, 'Testosterone', *Wikipedia, The Free Encyclopedia*, 25 Nov. 2008, 07:04 UTC; and Wikipedia contributors, 'Hypogonadism', *Wikipedia, The Free Encyclopedia*, 28 Nov. 2008, 11:56 UTC.

Phosphatidylserine, lysophosphatidylserine, and/or salts thereof can be administered to a subject having hypogonadism by a variety of methods including, for example, oral administration, intraveneous (IV) administration, parenteral administration, or a combination thereof. Preferably, phosphatidylserine, lysophosphatidylserine, and/or salts thereof are administered by oral administration.

Phosphatidylserine, lysophosphatidylserine, and/or salts thereof can be administered to a subject having hypogonadism at a convenient daily dosage. In certain embodiments, at most 600 mg per day of phosphatidylserine, lysophosphatidylserine, and/or salts thereof are administered to the subject. In certain embodiments, at least 100 mg per day of phosphatidylserine, lysophosphatidylserine, and/or salts thereof are administered to the subject. In certain embodiments, 500 mg per day of phosphatidylserine, lysophosphatidylserine, and/or salts thereof are administered to the subject. In certain embodiments, 400 mg per day of phosphatidylserine, lysophosphatidylserine, and/or salts thereof are administered to the subject. In certain embodiments, 300 mg per day of phosphatidylserine, lysophosphatidylserine, and/or salts thereof are administered to the subject. In certain embodiments, 200 mg per day of phosphatidylserine, lysophosphatidylserine, and/or salts thereof are administered to the subject.

The daily dosage of phosphatidylserine, lysophosphatidylserine, and/or salts thereof to a subject having hypogonadism can be administered in a single dose. Alternatively, the daily dosage of phosphatidylserine, lysophosphatidylserine, and/or salts thereof can be administered in multiple doses. For example, in certain embodiments phosphatidylserine, lysophosphatidylserine, and/or salts thereof are administered in at least two doses per day. For another example, in certain embodiments phosphatidylserine, lysophosphatidylserine, and/or salts thereof are administered in at least three doses per day.

Phosphatidylserine, lysophosphatidylserine, and/or salts thereof can be administered to a subject having hypogonadism for a convenient treatment period. In certain embodiments, phosphatidylserine, lysophosphatidylserine, and/or salts thereof can be administered to the subject for at least a one day treatment period. In certain other embodiments, phosphatidylserine, lysophosphatidylserine, and/or salts thereof can be administered to the subject for at least a 2 day, at least a 3 day, at least a 4 day, at least a 7 day, or at least a 10 day treatment period. In certain embodiments the treatment period can continue as needed (e.g., for life). In certain embodiments, phosphatidylserine, lysophosphatidylserine, and/or salts thereof can be administered to the subject for at most a one year treatment period. In certain other embodiments, phosphatidylserine, lysophosphatidylserine, and/or salts thereof can be administered to the subject for at most a 180 day, at most a 120 day, at most a 90 day, at most a 60 day, at most a 30 day, or at most a 15 day treatment period. In certain embodiments, phosphatidylserine, lysophosphatidylserine, and/or salts thereof can be administered to the subject for a 10 to 15 day treatment period.

Optionally, one or more exercise regimens as described herein can be implemented during at least a portion of the treatment period.

In certain embodiments, administration of phosphatidylserine, lysophosphatidylserine, and/or salts thereof to a subject having hypogonadism achieves an increase in testosterone (e.g., free testosterone and/or total testosterone) of at least 10%, at least 15%, at least 20%, at least 25%, at least 30%, at least 35%, at least 40%, at least 45%, at least 50%, or even higher than the testosterone level prior to administration of phosphatidylserine, lysophosphatidylserine, and/or salts thereof.

The present disclosure is illustrated by the following examples. It is to be understood that the particular examples, materials, amounts, and procedures are to be interpreted broadly in accordance with the scope and spirit of the disclosure as set forth herein.

EXAMPLES

Example 1

The Effects of Phosphatidylserine on Endocrine Response to Moderate Intensity Exercise The purpose of the current study was to investigate the efficacy of short-term S-PS supplementation, at dosage levels less than the currently established dose, on testosterone response to acute moderate-intensity exercise. This study aimed to examine the influence of short-term supplementation with a moderate dose of PS (600 mg per day) on plasma concentrations of testosterone before, during, and following moderate intensity exercise in healthy males. 10 healthy male subjects participated in the study. Each subject was assigned to ingest 600 mg PS or placebo per day for 10 days using a double-blind, placebo-controlled, crossover design. Serial venous blood samples were taken at rest, after a 15 minute moderate intensity exercise protocol on a cycle ergometer that consisted of five 3-minute incremental stages beginning at 65% and ending at 85% $VO_{2max}$, and during a 65 minute passive recovery. Plasma samples were assessed for testosterone for treatment (PS or placebo). PS increased AUC for testosterone to cortisol ratio (184±5%) when compared to placebo (p<0.05).

The findings suggest that PS is an effective supplement for combating exercise induced stress and preventing the physiological deterioration that can accompany too much exercise. PS supplementation can also promote a desired hormonal status for athletes by increasing testosterone levels.

Methods

Subjects. Ten healthy males participated in this study. All subjects in this investigation participated in a familiarization session. During the familiarization session, subjects were informed as to the experimental procedures, completed a personal/medical history form, and signed informed consent statements in adherence with the human subject's guidelines of the American College of Sports Medicine. Subject characteristics are presented in Table 1. No subject in this trial was a vegetarian with all subjects reportedly consuming meat in their daily diet.

TABLE 1

Subject characteristics (values are mean ± SEM).

| Characteristic | N = 10 |
|---|---|
| Age (years) | 26.2 ± 1.5 |
| Bodyweight (kg) | 89.3 ± 4.7 |
| Height (cm) | 176.8 ± 2.7 |
| Peak $VO_{2max}$ (ml/kg/min) | 29.0 ± 2.2 |

Experimental Design

Each participant completed three testing sessions during the 21-day study. Participants performed a graded exercise test (starting at 50 W, increasing by 50 W increments every 2 minutes) on a cycle ergometer (Gary Fisher Tarpon OS Series Mountain Bike connected to a Computrainer Pro model 8002 RacerMate EBRA™ Approved System with software version 1.1.59) to assess maximal oxygen consumption ($VO_{2max}$), and were scheduled for testing sessions 2 and 3 (day 11 and day 21). $VO_{2max}$ was determined using a Sensormedic V229 Metabolic System that was calibrated following the recommended technical guidelines (Sensormedics Corporation, Yorba Linda, Calif.). Upon completion of the $VO_{2max}$ test the participants were randomly assigned to one of two groups and received a 10-day supply of either the placebo or PS (600 mg per day of soy-derived PS).

The second and third exercise sessions were performed to determine testosterone responses to exercise induced stress at rest, during exercise, and recovery. On the tenth day of supplementation the participants ingested the last dose of the assigned substance (PS or placebo) and reported to the laboratory at 7 am after an overnight fast. Venous blood samples were taken on arrival (−30) and 30 minutes later, which was just prior to the start of exercise (0). Following the 30 minute rest period, the participants were asked to begin exercising on the cycle ergometer at an exercise intensity calculated to elicit 65% of $VO_{2max}$. The intensity of exercise was increased automatically by 5% every 3-minute increment until the intensity was at 85% of $VO_{2max}$ (five-three minute stages). After cycling for a total of 15 minutes, the subject stopped exercising and a post-exercise venous blood sample was taken immediately. The participant was then moved to an examination table during the remaining 65 minutes of the recovery phase and venous blood samples were taken at 5, 15, 25, 45 and 65 minutes post-exercise (+20, +30, +40, +60, +80). During the rest, exercise, and recovery portion of the study the participant was allowed to intake water ad libitum. Upon completion of the first experimental session the participant was given the other supplement treatment and repeated the previously described protocol 10 days later.

The PS and placebo (maltodextrin) supplements were administered in the form of chocolate flavored chewable tablets that were obtained from SwissCo Development AG (Sisseln, Switzerland). The subjects received a 10-day supply of each supplement after completing the $VO_{2max}$ test and the second exercise session.

Blood Analysis

The serial blood samples were taken from an antecubital vein and collected into 10 ml tubes containing lithium heparin, subsequently centrifuged and the plasma was harvested. Separate aliquots of plasma (~500 μl) were stored frozen at −80° C. prior to analysis for free testosterone. Plasma concentrations of testosterone were analyzed in duplicate via enzyme immunoassay (EIA) and GH concentrations were analyzed in duplicate via enzyme-linked immunosorbant assay (ELISA) using commercial available kits (Diagnostic Systems Laboratories, Inc., Webster, Tex.). The YSI 1500 SPORT Lactate Analyzer (YSI Incorporated, Yellow Springs, Ohio) was used to measure plasma lactate concentrations in duplicate.

Statistical Analysis

The statistical package used to analyze assay data results was SPSS software version 10.0 for Windows (SPSS Inc., Chicago, Ill.). The determination of the sample size and effect size was appropriate for the number of treatments in this type of research and was consistent with research conducted by Monteleone et al. (Eur J Clin Pharmacol 1992, 42:385-388), Fahey et al. (Biol Sport 1998, 15:135-144), and Hinkle et al. (Applied Statistics for the Behavioral Sciences (4$^{th}$ ed.). Boston, Mass.: Houghton Misslin Company; 1998). Pre- and post-supplementation test measures were assessed for testosterone using a two-way univariate repeated measures analysis of variances (ANOVA) for treatment (soy PS, placebo) by time (−30, 0, 15, 20, 30, 40, 60, & 80 minutes). In addition, the area under the curve (AUC) was calculated via integral calculus for testosterone.

Results

FIG. 1 shows the effects of S-PS or placebo supplementation on testosterone response to exercise induced stress at −30, 0, 15, 20, 30, 40, 60, and 80 minutes after exercise. Mean peak concentrations of testosterone (ng/ml) were 8.3±1.7 for S-PS supplementation, 5.5±0.3 for placebo supplementation, with a P value (treatment) of 0.13.

S-PS supplementation resulted in higher plasma testosterone levels at the beginning of the exercise when compared to placebo.

Plasma testosterone concentrations increased with S-PS (51±6%) when compared with placebo.

Figure 2:
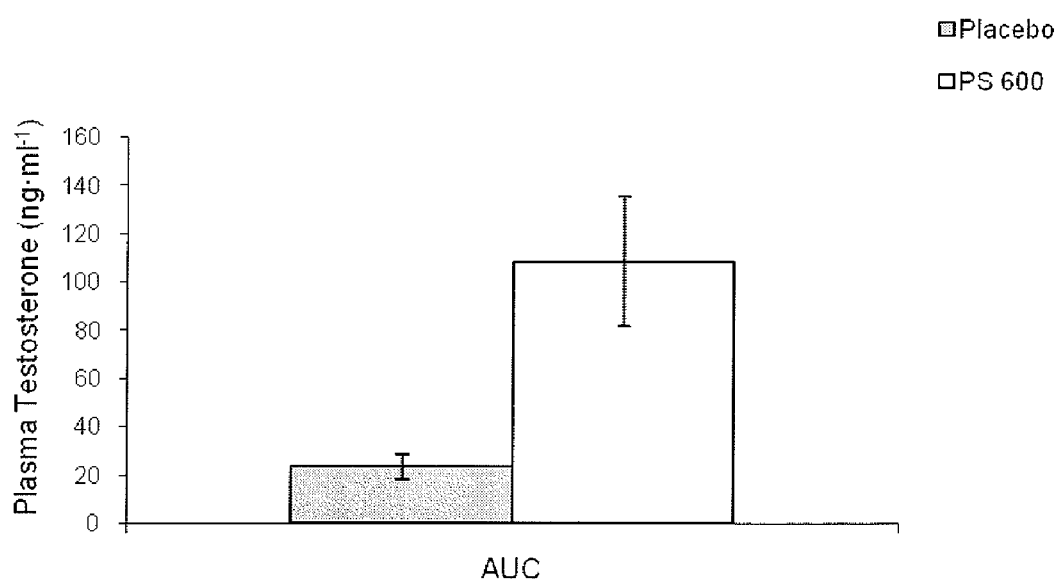
FIG. 2 illustrates a significant difference in plasma testosterone response area under the curve (AUC) between the placebo and 600 mg/day soy-derived phosphatidylserine (S-PS) group.

S-PS supplementation resulted in a favorable physiological state when compared to the placebo group. Area under the curve analysis (FIG. 2) showed significant differences between S-PS and placebo for testosterone (37±5% increase, p=0.02).

Conclusion

PS supplementation with 600 mg per day for 10 days increases the testosterone levels. These findings suggest that PS is an effective supplement for combating exercise induced stress. PS supplementation promotes a desirable hormonal balance for athletes and might attenuate the physiological deterioration that accompanies overtraining and/or overstretching.

Example 2

Effect of PS Supplementation on Older Males

The results found with healthy mid-twenties males suggested a study to determine whether older men would respond to PS supplementation to raise testosterone levels.

A. A 53 year old subject (SH), a physically active non smoking male who took no prescription drugs or alcohol was the first subject. Starting on Day 1, SH consumed 600 mg of Phosphatidylserine (Chemi Nutra, Inc., White Bear Lake, Minn.) for 11 days accompanied by the following cardio and resistance workouts:

Day 1: lifted weights for 1.5 hours and intense cardio exercise, 12 minutes.
Day 2: intense cardio exercise for 28 minutes.
Day 3: easy pace walk, 1.5 mile.
Day 4: intense cardio exercise for 35 minutes.
Day 5: easy pace walk, 2 miles.
Day 6: lifted weights for 1.5 hours.
Days 7 and 8: rest, no exercise.
Day 9 intense cardio exercise, 35 minutes and 12 miles easy pace walk
Day 10: lifted weights 1.5 hours.

Blood was drawn at 8:00 am on the first and eleventh day of the study and analyzed for serum and free testosterone by Life Extension National Diagnostics, Inc., Ft. Lauderdale, Fla. Serum testosterone rose from 575 nanograms per decilitier to 665 nanograms per deciliter, a 16% increase.

B. The second subject (RJ) is a 39 year old male. Starting on day 1, RJ consumed 400 mg PS daily for 11 days, accompanied by the following exercise regimens:

Day 2: bicycle ergometer for 30 minutes and elliptical trainer for 30 minutes.
Day 3: tennis singles match for 1.5 hours.
Day 4: treadmill 15 minutes and upper body resistance exercise for 1 hour.
Day 5: elliptical trainer for 45 minutes and resistance exercise for 30 minutes.
Day 6: rest.
Day 7: treadmill for 30 minutes; elliptical trainer for 30 minutes; resistance exercise for 30 minutes.
Day 8: rest.
Day 9: resistance exercise 1.5 hours.
Day 10 elliptical trainer for 1 hour.
Day 11: upper body resistance exercise for 30 minutes.

Serum testosterone levels and free testosterone levels were measured on days 1 and 12. Serum testosterone increased from 290 nanograms/deciliter to 437 nanograms/deciliter, an increase of 51%. Free testosterone increased from 11.4 picograms/ml to 18.0 picograms/ml, an increase of 58%.

C. The third subject is a 40 year-old man (MP). MP consumed 300 mg PS (Chemi Nutra) daily for 11 days accompanied by a cardio and resistance training workout on days 2-11:

Day 2: 9 miles cycling for 35 minutes; 4 miles running for 40 minutes; 9 miles cycling for 40 minutes.
Day 3: tennis singles match for 1.5 hours.
Day 4: 9 miles cycling for 45 minutes; whole body resistance training for 1 hour; 9 miles cycling for 50 minutes.
Day 5: 9 miles cycling for 30 minutes; 5 miles running for 45 minutes; 9 miles cycling for 30 minutes
Day 6: rest.
Day 7: rest.
Day 8: resistance training 1.5 hours.
Day 9: 9 miles cycling for 50 minutes; upper body resistance exercise 1 hour; 9 miles cycling for 50 minutes.
Day 10: high-intensity resistance training for 30 minutes.
Day 11: 5 miles running for 50 minutes.

Serum testosterone levels and free testosterone levels were measured on days 1 and 12. Serum testosterone increased from 734 nanograms/deciliter to 781 nanograms/deciliter, an increase of 6.4%. Free testosterone increased from 22.1 picograms/ml to 27.0 picograms/ml, an increase of 22%.

The complete disclosure of all patents, patent applications, and publications, and electronically available material (e.g., GenBank amino acid and nucleotide sequence submissions; and protein data bank (pdb) submissions) cited herein are incorporated by reference. The foregoing detailed description and examples have been given for clarity of understanding only. No unnecessary limitations are to be understood therefrom. The disclosure is not limited to the exact details shown and described, for variations obvious to one skilled in the art will be included within the invention defined by the claims.

What is claimed is:

1. A method for increasing the testosterone level of a subject having an age related decline in testosterone, the method comprising administering to the subject in need thereof by oral ingestion, 100 mg to 600 mg per day of an agent for increasing testosterone level, the agent consisting of one or more lipids selected from the group consisting of phosphatidylserine, a salt of phosphatidylserine, lysophosphatidylserine, and a salt of lysophosphatidylserine.

2. The method of claim 1 wherein the subject is a human male.

3. The method of claim 2 wherein the one or more lipids are derived from plants.

4. The method of claim 3 wherein the lipid is phosphatidylserine derived from soy.

5. The method of claim 4 wherein the phosphatidylserine is administered to the subject for a 10 to 15 day treatment period.

6. The method of claim 5 wherein the phosphatidylserine is administered in at least two doses per day.

7. The method of claim 2 further comprising subjecting the subject to an exercise regimen for at least a portion of the treatment period.

8. The method of claim 2 wherein the testosterone level is increased by at least 10% over the testosterone level prior to administration of the composition.

9. A method for increasing the testosterone level of a subject having an exercise induced decline in testosterone, the method comprising administering to the subject in need thereof by oral ingestion, 100 mg to 600 mg per day of an agent for increasing testosterone level, the agent consisting of one or more lipids selected from the group consisting of phosphatidylserine, a salt of phosphatidylserine, lysophosphatidylserine, and a salt of lysophosphatidylserine.

10. The method of claim 9 wherein the subject is a human male.

11. The method of claim 10 wherein the lipid is phosphatidylserine derived from soy.

12. The method of claim 11 wherein the phosphatidylserine is administered to the subject for 10 to 15 days.

13. The method of claim 10 wherein the testosterone level is increased by at least 10% over the testosterone level prior to administration of the composition.

* * * * *